United States Patent
Munn

(10) Patent No.: US 10,639,394 B2
(45) Date of Patent: May 5, 2020

(54) DISINFECTING VANITY CABINET

(71) Applicant: STERILUMEN, INC., Tarrytown, NY (US)

(72) Inventor: Max Munn, Tarrytown, NY (US)

(73) Assignee: SteriLumen Inc., Tarrytown, NY (US)

(*) Notice: Subject to any disclaimer, the term of this patent is extended or adjusted under 35 U.S.C. 154(b) by 0 days.

(21) Appl. No.: 16/268,715

(22) Filed: Feb. 6, 2019

(65) Prior Publication Data
US 2019/0175780 A1 Jun. 13, 2019

Related U.S. Application Data

(63) Continuation of application No. 16/173,164, filed on Oct. 29, 2018, now Pat. No. 10,456,496, and a (Continued)

(51) Int. Cl.
*A61L 9/20* (2006.01)
*A61L 2/26* (2006.01)
(Continued)

(52) U.S. Cl.
CPC .............. *A61L 9/20* (2013.01); *A47B 67/005* (2013.01); *A47G 1/02* (2013.01); *A61L 2/10* (2013.01);
(Continued)

(58) Field of Classification Search
CPC .................................. A61L 2/10; A45D 42/00
(Continued)

(56) References Cited

U.S. PATENT DOCUMENTS 2,758,900 A * 8/1956 Marchand .............. A45C 15/06
312/223.5
3,776,694 A * 12/1973 Leittl ........................ A61L 2/10
422/24

(Continued)

FOREIGN PATENT DOCUMENTS

CN 202526007 11/2012
CN 202629828 12/2012
(Continued)

OTHER PUBLICATIONS

UV Antimicrobial Devices Used to Combat HAIs in Medical Facilities http://www.iuvanews.com/stories/122716/uv-antimicrobial-devics-used-combat-hais.shtml.

*Primary Examiner* — Michael Maskell
(74) *Attorney, Agent, or Firm* — Myron Greenspan; Lackenbach Siegel LLP

(57) ABSTRACT

A vanity mirror comprising a substantially enclosed cabinet having top, bottom and lateral ends and rear and front walls when mounted on a wall, said cabinet ends and said walls together forming a substantially enclosed space defining a vertical direction extending between said top and bottom ends, said front wall comprising a mirror panel; mounting means for mounting said cabinet on a wall, wherein said mounting means includes a hinge at one of said lateral ends to movably mount said cabinet for movement between a normally closed position substantially juxtaposed against the wall and an open position to provide access to a surface normally covered by said cabinet, when in said closed position, whereby said normally covered surface can be cleaned and disinfected.

11 Claims, 9 Drawing Sheets

Related U.S. Application Data continuation-in-part of application No. 16/057,433, filed on Aug. 7, 2018, now Pat. No. 10,463,759, and a continuation of application No. 15/601,607, filed on May 22, 2017, now Pat. No. 10,039,853, and a continuation of application No. 15/418,231, filed on Jan. 27, 2017, now Pat. No. 9,724,442.

(51) Int. Cl.

| | | |
|---|---|---|
| *A61L 2/10* | (2006.01) | |
| *A47B 67/00* | (2006.01) | |
| *A47G 1/02* | (2006.01) | |
| *A47G 1/06* | (2006.01) | |

(52) U.S. Cl.
CPC ......... *A61L 2/26* (2013.01); *A47B 2220/0091* (2013.01); *A47G 1/0622* (2013.01); *A61L 2202/11* (2013.01); *A61L 2202/14* (2013.01); *A61L 2202/26* (2013.01); *A61L 2209/111* (2013.01); *A61L 2209/12* (2013.01); *A61L 2209/15* (2013.01)

(58) Field of Classification Search
USPC ................ 250/423 R, 435, 504 R, 492.1
See application file for complete search history.

(56) References Cited

U.S. PATENT DOCUMENTS

| | | | |
|---|---|---|---|
| 6,773,682 B1 | 8/2004 | Benda | |
| 7,600,886 B1* | 10/2009 | Sullivan | A47G 1/02 312/223.5 |
| 8,193,515 B2* | 6/2012 | Kreitenberg | A61L 2/10 250/455.11 |
| 8,662,705 B2 | 3/2014 | Roberts | |
| 8,779,385 B2 | 7/2014 | Noori | |
| 8,900,518 B2 | 12/2014 | Seck | |
| 9,308,289 B2* | 4/2016 | Graff | A61L 9/20 |
| 9,480,768 B2 | 11/2016 | Krosney et al. | |
| 9,724,442 B1* | 8/2017 | Munn | A61L 2/10 |
| 2002/0098127 A1* | 7/2002 | Bollini | A61L 9/20 422/121 |
| 2007/0053188 A1 | 3/2007 | New et al. | |
| 2008/0008620 A1* | 1/2008 | Alexiadis | A61L 2/10 422/24 |
| 2008/0170309 A1* | 7/2008 | Helenowski | A47G 1/02 359/839 |
| 2009/0041538 A1* | 2/2009 | Berger | E06B 3/9684 403/231 |
| 2009/0291029 A1 | 11/2009 | Ogasawara | |
| 2010/0097013 A1* | 4/2010 | Inskeep | A61L 2/10 315/360 |
| 2010/0296298 A1* | 11/2010 | Martin, Jr. | A45D 42/10 362/311.06 |
| 2012/0199005 A1 | 8/2012 | Koji et al. | |
| 2012/0261593 A1* | 10/2012 | Noori | A61L 2/10 250/492.1 |
| 2013/0214174 A1* | 8/2013 | Domenig | A61L 2/10 250/455.11 |
| 2014/0060104 A1* | 3/2014 | Shur | A61L 2/10 62/264 |
| 2015/0320209 A1* | 11/2015 | Hasselback | H04N 5/2251 348/151 |
| 2015/0360606 A1 | 12/2015 | Thompson et al. | |
| 2016/0074546 A1* | 3/2016 | Rizzone | A61L 2/10 250/455.11 |
| 2017/0007736 A1 | 1/2017 | Engelhard | |
| 2017/0105554 A1* | 4/2017 | Forrest | A47G 1/1686 |
| 2017/0202988 A1* | 7/2017 | Clark | A61L 2/10 |
| 2018/0214595 A1 | 8/2018 | Munn | |

FOREIGN PATENT DOCUMENTS

| | | |
|---|---|---|
| CN | 202908345 | 1/2013 |
| CN | 203633880 | 6/2014 |
| CN | 104524607 | 4/2015 |
| CN | 205561091 | 9/2016 |
| KR | 20120133286 | 12/2012 |

* cited by examiner

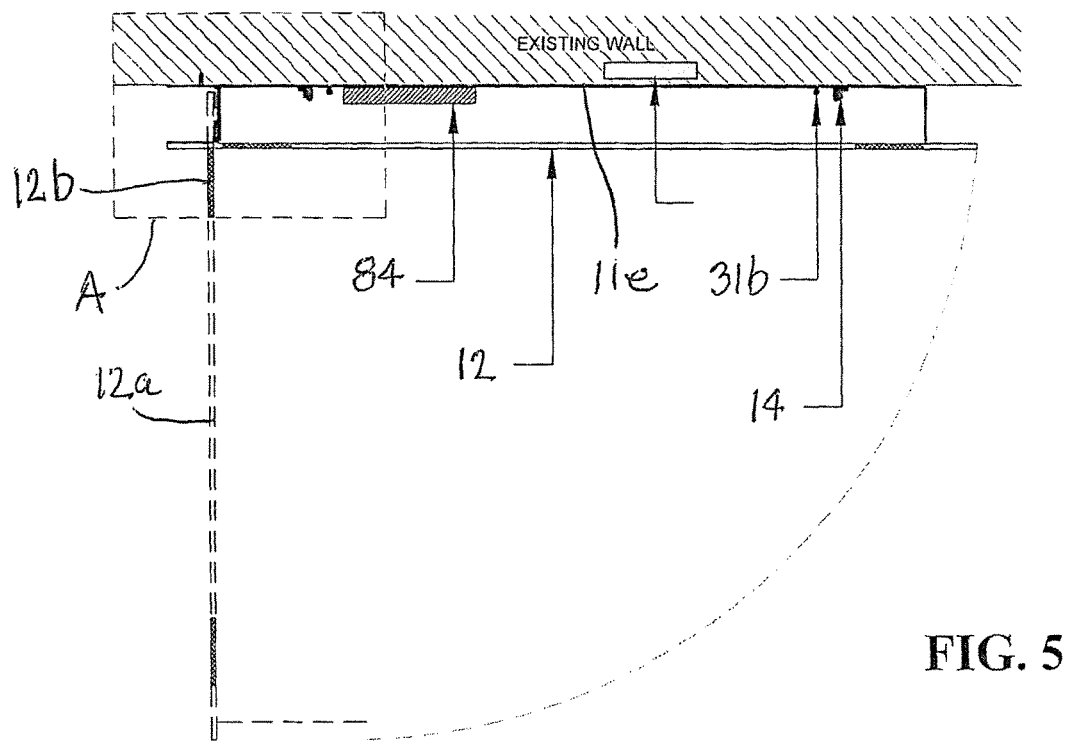
FIG. 5
FIG. 6
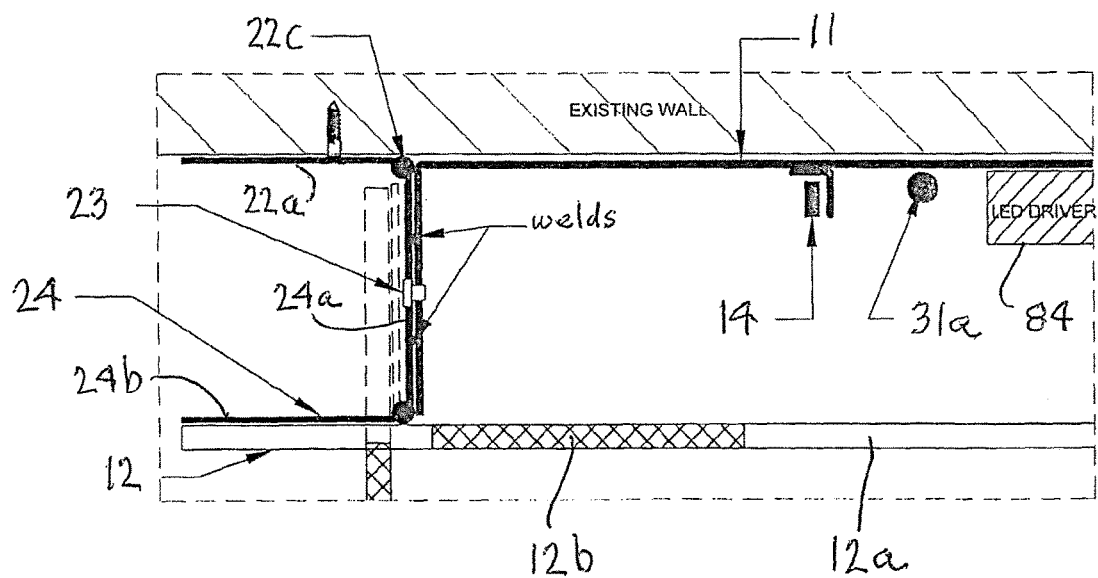

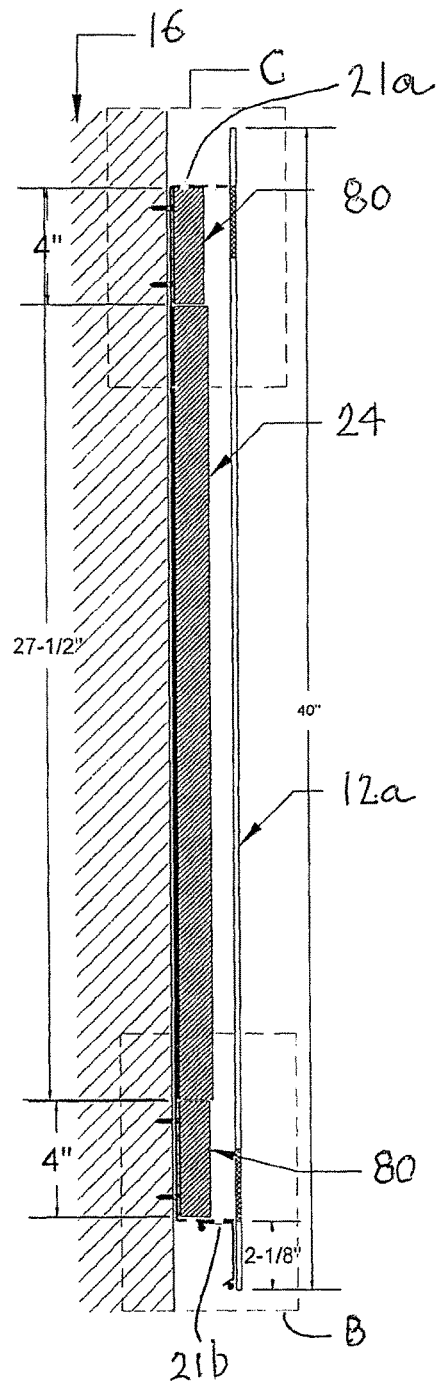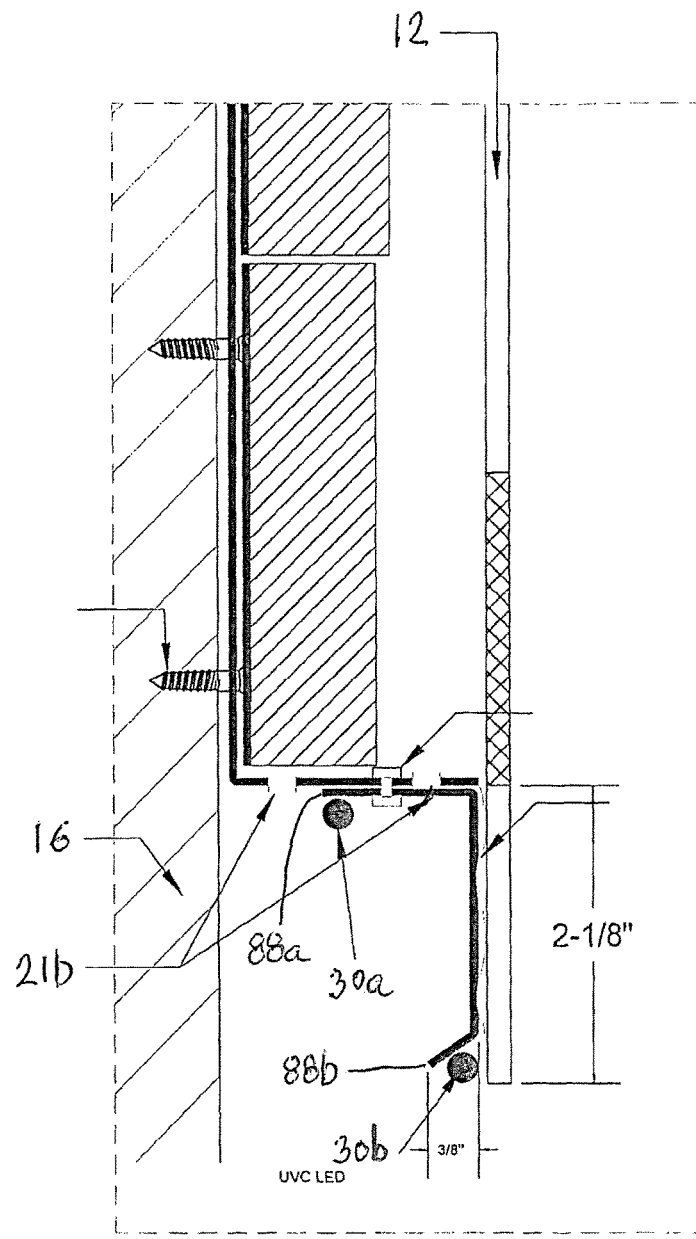
FIG. 7
FIG. 8

DISINFECTING VANITY CABINET

CROSS REFERENCE TO RELATED APPLICATIONS

This application is a continuation of U.S. patent application Ser. No. 16/173,164, filed Oct. 29, 2018 for System and Method of Disinfecting Surfaces Within and Around Vanity Mirrors, which is a continuation-in-part of U.S. patent application Ser. No. 16/057,433, filed Aug. 7, 2018 for Disinfecting Vanity Mirrors, which is a continuation-in-part of U.S. patent application Ser. No. 15/601,607, filed May 22, 2017 for Hazard-Free Disinfecting Vanity Mirrors issued as U.S. Pat. No. 10,039,853, which is a continuation-in-part of U.S. patent application Ser. No. 15/418,231 for Disinfecting Vanity Mirror issued as U.S. Pat. No. 9,724,442 all of which are hereby incorporated herein by reference.

BACKGROUND OF THE INVENTION

1. Field of the Invention

This invention generally relates to vanity mirrors and, more specifically, to vanity mirrors that are hingedly mountable on a support surface to be movable between a normal retracted position in proximity to the support surface and an extended position that exposes and provides access to the support surface so that it can be cleaned and/or disinfected.

2. Description of the Background Art

Health care-acquired infections (HAIs) in hospitals, assisted living facilities, etc., are serious health problems. It has been estimated that HAIs cause or contribute in excess of 99,000 deaths annually in the United States. The Center for Disease Control (CDC) reports 1 in 25 patients will contract at least one infection during their stay. Various bacteria become immune or resistant to disinfectants applied to surfaces in hospitals and other medical facilities, these bacterias commonly cause what are being referred to as "staph" infections because they are resistant to many chemical disinfectants used to clean counter tops and other surfaces in hospital rooms and the like. The general problem is discussed, for example, in the Official Publication of the International Ultra Violet Association, IUVANews. http://www.iuva.org/Publications. These infections are considered preventable. In 2011 the federal government stopped reimbursing hospitals for the care of patient that acquired an infection during their stay. Additional penalties for high infection rates have since been added that are in some situations as much as 40% of the overall revenue.

One of the hurdles to success are multi drug resistant organisms (MDRO) that are resistant to standard disinfection products and practices. This has opened the door for new technologies such as ultraviolet germicidal irradiation (UVGI) that primarily uses short-wavelength ultraviolet (UV-C) light to kill or inactivate microorganisms such as bacteria, viruses, molds and other pathogens.

Each year over 1,400,000 patients contract diseases unrelated to their initial stay at a hospital. Approximately 100,000 Americans die each year for this reason. The cost, both emotionally and financially is staggering and difficult to calculate.

The greatest concentration of pathogens within a hospital room occurs at the surface in the area surrounding the sink in the bathroom. Specifically, the faucet and the handles and the surface between these controls, and the back splash behind the sink, including the wall surface just above the sink is the most infected area in the typical hospital room.

Various UV devices have been proposed to reduce infectious pathogens. For example, bathrooms in airplanes have started to use UV LED strips to reduce pathogens while in flight. Other facilities are being outfitted with various devices to expose pathogens to UV light sources. However, UV light sources have generally been independent or stand alone devices that are specifically designed for intermittent applications. Vanity mirrors, including backlit mirrors mounted on cabinets or housings mountable on a support surface, are generally fixedly mounted to the support surface so that the mirrors cannot be moved and the support surfaces behind the mirrors serve as breeding grounds or havens for pathogens but are not accessible for cleaning and/or disinfecting to eliminate bacteria and/or other pathogens.

SUMMARY OF THE INVENTION

In order to address the above and other problems associated with sanitizing or sterilizing airborne pathogens it is an object of the invention to provide a disinfecting vanity mirror that can be easily, quickly and conveniently moved away from a support surface to expose pathogens that can and do proliferate and accumulate on such support surfaces, that are normally covered by vanity mirror cabinets, so that the support surface can be cleaned with a disinfectant to destroy or neutralize such pathogens and makes them ineffective or less effective.

It is another object of the invention to provide a disinfecting vanity mirror as in the previous object that is simple in construction and economical to manufacture.

It is still another object of the invention to provide a disinfecting vanity mirror as in the previous objects that is simple and convenient to install above sinks, countertops and other areas in medical and other facilities that require sanitary conditions.

It is yet another object to the invention to provide a backlit vanity mirror that is hingedly mounted to allow the mirror, including any cabinet or housing for the mirror, to be moved between a normal position against a support surface, such as a wall, and an extended position to expose substantially the entire, normally covered support surface for cleaning and/or disinfecting to sanitize the surface and eliminate or substantially reduce bacteria and other pathogens thereon.

It is an additional object to pivotally mount a vanity mirror cabinet along one vertical edge, side or end so that it can be easily pivoted and, with little effort, moved away from the normally covered or hidden mounting surface to provide access for cleaning and/or disinfecting.

A vanity mirror in accordance with the invention, that can include a backlit mirror, comprises a substantially enclosed cabinet having top, bottom and lateral ends and rear and front walls when mounted on a wall, said cabinet ends and said walls together forming a substantially enclosed space defining a vertical direction extending between said top and bottom ends. Said front wall comprises a mirror panel. Mounting means is provided for mounting said cabinet on a wall, said mounting means including a chassis hinge at one of said one lateral ends to movably mount said cabinet between a normally closed position substantially juxtaposed against the wall and an open position to provide access to a surface normally covered by said cabinet when in said closed position, whereby said normally covered surface can be cleaned, disinfected and/or sanitized.

BRIEF DESCRIPTION OF THE DRAWINGS

Those skilled in the art will appreciate the improvements and advantages that derive from the present invention upon reading the following detailed description, claims, and drawings, in which:

FIG. 5 is a top plan view of the mirror shown in FIGS. 3 and 4, with the mirror panel in a closed position, and, in phantom outline, in the open position to provide access to the interior of the cabinet;

FIG. 6 is an enlarged view of detail A shown in FIG. 5;

FIG. 7 is a side elevational view, in vertical section, of the cabinet shown in FIGS. 3 and 4;

FIG. 8 is an enlarged view of detail B shown in FIG. 7;

DESCRIPTION OF PREFERRED EMBODIMENTS

The twenty or so most prevalent and dangerous pathogens in hospitals that congregate around sinks and counter-top surfaces can be very significantly reduced when exposed to ultraviolet waves especially in the range of 260-280 nanometers, a fact that is now well documented. The UV diodes that generate this particular wave length (referred to as UVC waves) have in the last few years become commercially available.

The applicant of the subject application has developed a UV generating electrified wall mirror that is also a lighting fixture that is:
 a. Aesthetically acceptable;
 b. Easy to install;
 c. Provides 99.99% destruction of pathogens;
    when used for approximately 45 minutes over a 24-hour period;
 d. Entirely safe;
 e. The back of the unit is easily accessible for maintenance and cleaning; and
 f. Serves both as a wall mirror and a lighting fixture.

The unit is hinge-mounted, and somewhat similar to the permanently mounted, back lit electrified mirrors that applicant is currently selling to the hotel industry.

Figure 1:
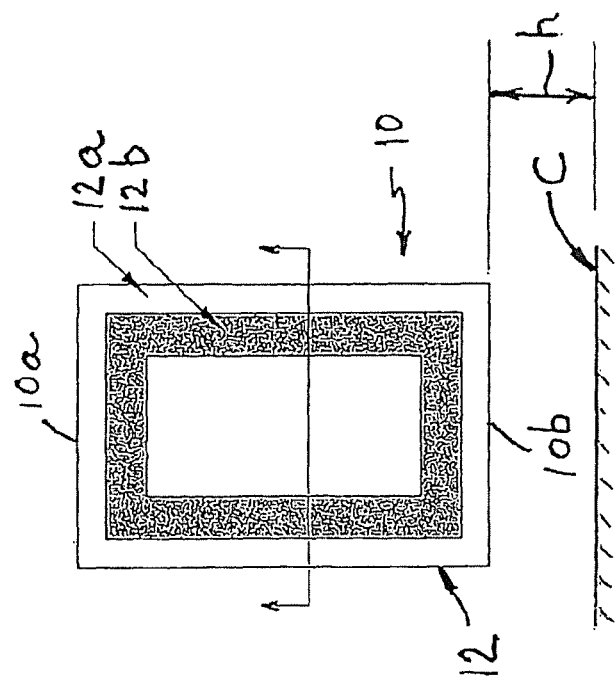
FIG. 1 is a front elevational view of a disinfecting vanity mirror in accordance with the present invention.
Figure 3:
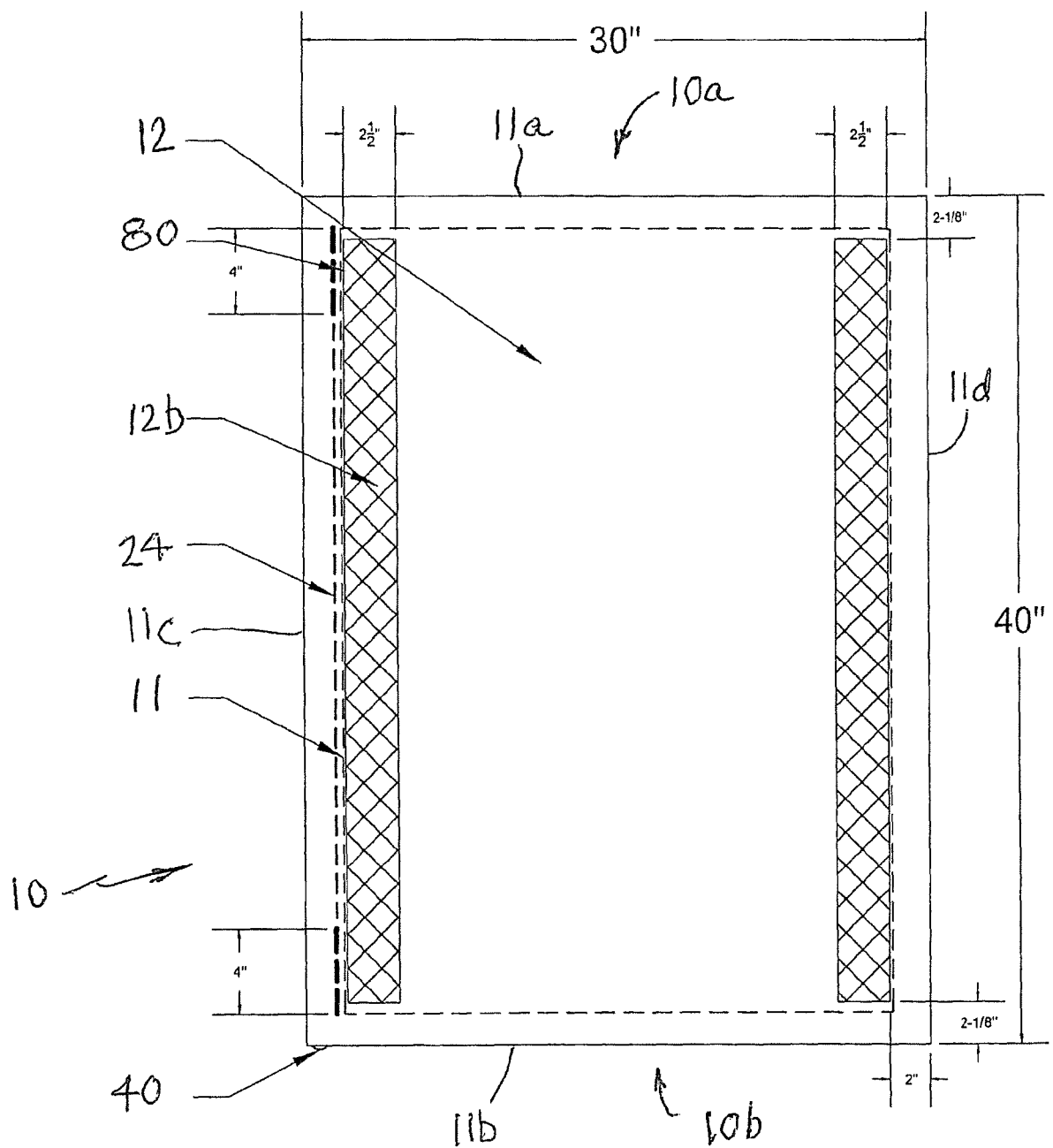
FIG. 3 is an enlarged front elevational view of the invention shown in FIGS. 1 and 2.

Referring now specifically to the figures, in which the identical or similar parts are designated by the same reference numerals throughout, and first referring to FIG. 1, one embodiment of a disinfecting vanity mirror in accordance with the invention is generally designated by the reference numeral 10.

The mirror 10 is generally rectangular in shape as shown and includes a top end 10a and a bottom end 10b. The mirror 10 includes a substantially enclosed cabinet 11 having top, bottom, left, right and rear walls 11a, 11b, 11c, 11d and 11e, respectively. The cabinet 11 also has a front wall in the form of a mirror panel 12 having a central reflective surface 12a and a frosted peripheral strip 12b. The mirror panel 12 may be 3/16" clear hospitality grade mirror. The mirror 10 may be similar in appearance to back-lit mirrors of the type manufactured by MunnWorks LLC in Mount Vernon, N.Y. The LED Strip 14 emits visible light, for example, at 2700 k that provides lighting through the frosted peripheral strip 12b in a conventional manner.

Figure 2:
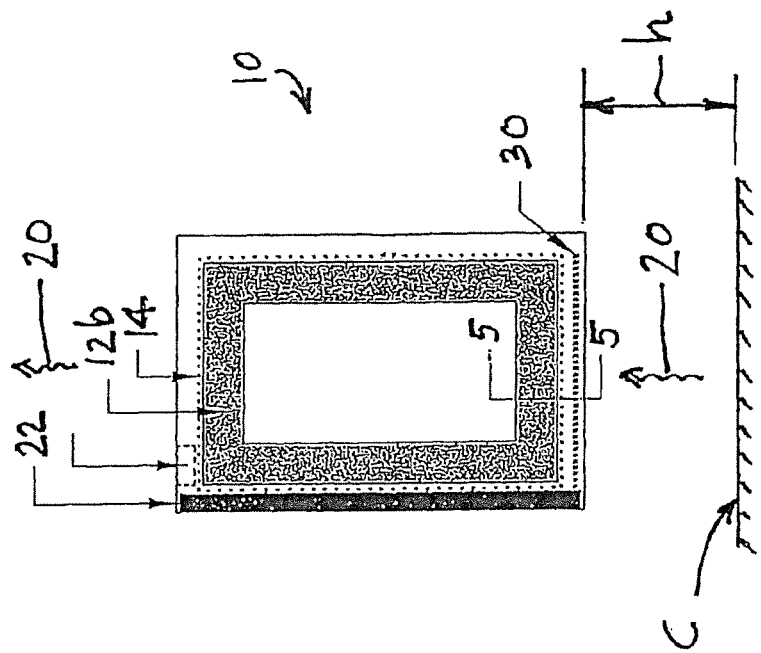
FIG. 2 is similar to FIG. 1 but shows additional details.

Referring to FIGS. 1, 2 and 5, the mirror 10 is typically mounted on a wall or vertical surface 16 above a countertop C. When mounted on the surface 16 the cabinet walls 11a-11e and the mirror panel 12 together form a substantially enclosed space or plenum 13 defining a vertical direction V (FIG. 1) extending between the top and bottom ends 10a, 10b between the mirror panel 12 and the mounting surface. The plenum space 13 according to the invention provides a substantially vertical air shaft, passageway or column for air to rise by entering through the bottom end 10b and exiting through the top end 10a as suggested by the arrows 20 in FIG. 2. Additional details will be provided below in connection with FIGS. 4, and 7-9. While the height of the mirror 10 above the countertop C is not critical a height of 10" is typical and will provide beneficial germicidal results in the application of the invention.

Referring specifically to FIGS. 3-11, a method of mounting the mirror 10 is illustrated. A chassis hinge or hanger 22 is provided that includes a first hinge plate 22a and a second hinge plate 22b, the two hinge plates being joined for relative pivotal rotation at 22c. As shown in FIGS. 5 and 6, the hinge plate 22a is generally coextensive with the wall 16 to which it is attachable while the hinge plate 22b is provided at one lateral wall for attachment thereto by any suitable fastener means, such as bolt or rivet 23. The hinge 23 may be a single long hinge such as a piano hinge, or a plurality of spaced smaller hinges along the associated lateral or side cabinet wall.

Figure 10:
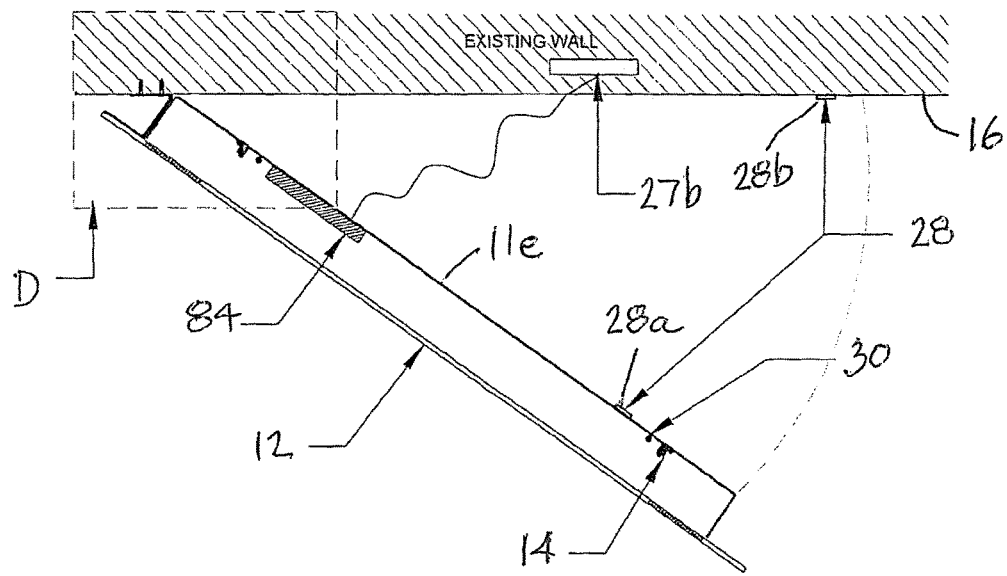
FIG. 10 is similar to FIG. 5, showing the cabinet in a pivoted extended position to provide access to the surface normally covered by or behind the cabinet.
Figure 11:
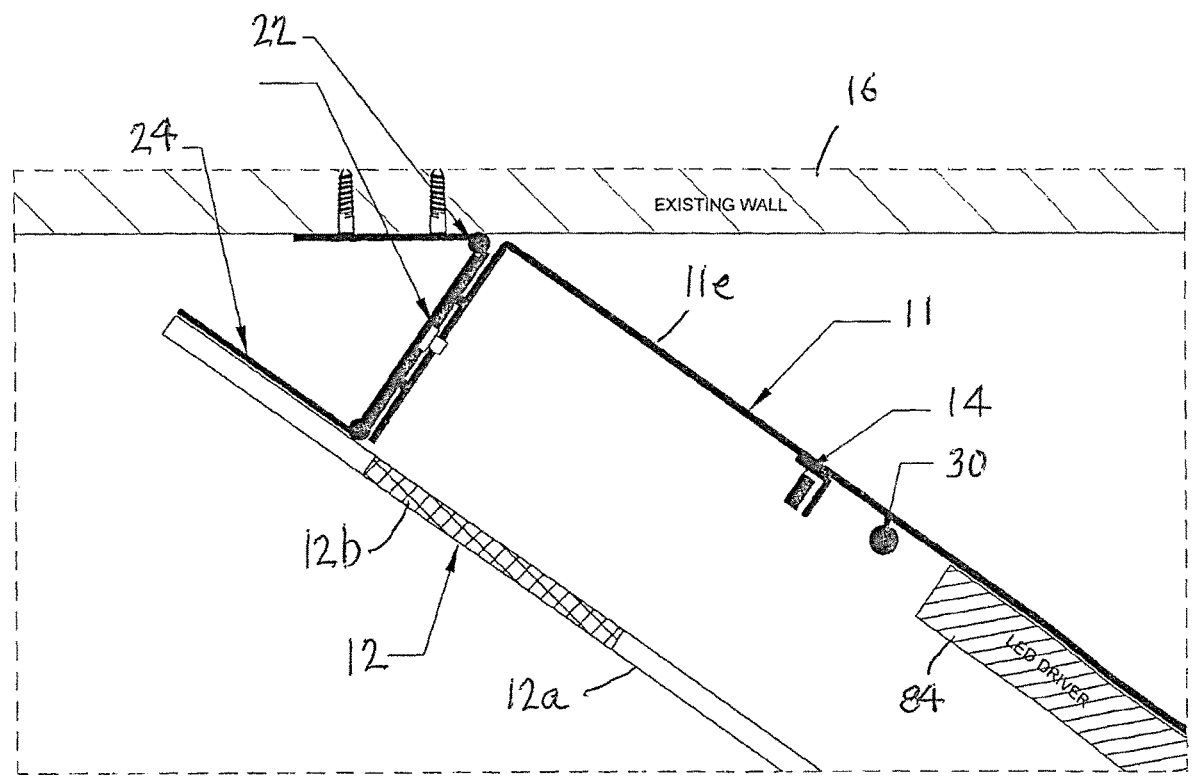
FIG. 11 is an enlarged view of detail D shown in FIG. 10.

Referring to FIG. 10, suitable means 28 is advantageously provided to prevent inadvertent movement of the cabinet 11 from its retracted position shown in FIGS. 5 and 6. Such means may include a magnet 28a mounted on the back of rear wall 11e and suitably positioned element 28b mounted on the wall 16 to register with the magnet 28a. The elements 28a, 28b can be interchanged as to where they are mounted. The cooperating element 28b may be another suitably polorized magnet or ferromagnetic disc or plate that is magnetically attracted to the magnet 28a.

Any suitable or conventional hinge can be used to mount the mirror panel 12. However, as shown in FIG. 6, a U-shaped plastic hinge 24 is preferred for this application to eliminate or minimize the number of interstices or crevasses in which pathogens can become lodged and multiply. A first portion 24a of the plastic hinge is secured to the hinge plate 22b while a second portion 24b is secured to the mirror panel 12.

A feature of the mirror 10 is the integration of a source of UV light 30 that extends along at least a portion but preferably along the entire width of the bottom end 10b to expose pathogens to UV radiation and the heat generated the LEDs also promotes convection of air and updraft efficiency by locally heating air proximate to the bottom end 10*b* to generate airflow 20 (FIG. 2). The UV light sanitizes air moving upwardly through the enclosed space or plenum space 13, created to simulate a chimney effect, and promote movement of air past the UV light source 30. Also, by providing the UV light source 30 in proximity to the lower end or edge of the mirror 10 the UV light will be efficient in sanitizing or neutralizing pathogens on the countertop C.

The UV light source 30 is in the form of a strip of LEDs that emit UV light within the range of 200-280 nm and, preferably within the range of 240-280 nm. As indicated in the IUVANews publication ultraviolet radiation is defined most broadly as consisting of radiation within the range of 10-400 nm. However, most effective for germicidal applications is the short wave ultraviolet light normally designated as UV-C. UV-C includes wavelengths of 100-280 nm, although 240-280 nm are most effective for sanitizing or sterilizing airborne pathogens. UV light in that range is most efficiently absorbed by DNA, with maximum absorption being at approximately 260 nm. UV-C has been used for air purification, sterilization and disinfection. High intensity UV at 240-280 nm radiation can destroy DNA in living micro organisms. The effectiveness of the UV radiation is directly related to the intensity and exposure time(s). The present disinfecting vanity mirror 10 is convenient, inexpensive and an effective way to neutralize micro-organisms and pathogens by constantly circulating and recycling the air that passes through the plenum space 13, forcing the air to be continuously exposed to the UV LED-strip 30.

To enhance the quantity of air moved through the plenum space 13 the mirror 10 may also advantageously utilizes a thermal strip 32, (not shown), for providing additional heating of the air in proximity to the UV LED strip 30 at the bottom end 10*b* of the mirror. Between the heating of the air by the UV LED strip 30 and a thermal strip the air below the vanity mirror 10 can be heated more quickly and more vigorously and to a higher temperature. This causes higher quantities of air to move up through the plenum space 13 thereby exposing increased numbers of pathogens to the UV light source 30.

By using a mirror 10, for example, that is 24-30" wide and 34-40" tall at a height of approximately 10" above a sink or countertop C most harmful pathogens can be neutralized if power is applied for only approximately 30 minutes per day. The LED strips are conventionally powered when a wall switch is turned on (e.g. in a bathroom where a sink, countertop and vanity mirror are typically situated). Normally the vanity is used for at least 30 minutes per day.

The disinfecting vanity mirror 10 is, therefore, an inexpensive and reliable way of exposing air contaminated with pathogens to UV-C light on an ongoing or continuing basis when energized to increase the effectiveness of the sanitization and decontamination of airborne and surface of microorganisms found on countertops.

By locating the UV light source 30 along the bottom edge of the mirror, behind the mirror panel 12, a number of advantages are achieved. The user is protected from UV radiation that can be harmful to the user's eyes and skin. Also, the light does not reflect onto the mirror to avoid undesirable shades or tones or lighting distortions. Using LED light strips considerably increases the life of the sources over conventional UV sources, such as mercury lamps or bulbs. By integrating the UV light source into the vanity mirror there is no need to have an operator use specialized UV equipment to periodically sanitize a facility.

The method of using the mirror 10 is to position a mirror panel 12 a predetermined space from a wall of a medical facility, work space or other chamber where vanity mirrors are utilized to create a plenum space 13 behind the mirror. UV light is then provided at the lower end of the mirror to heat the air and cause it to rise through the plenum space and expose pathogens in the air to the UV light in the range of 10-400 nm and generally 240-280 nm. An optimum wavelength is in the range of 260-270 nm for maximum effectiveness.

The method advantageously includes the additional step of providing enhanced heating of the air to promote movement of the air through the plenum space. This accelerates exposure of the air to be disinfected or sterilized to the UV light. This can be achieved by placing a thermal strip at the lower end of the mirror.

An additional UV-LED strip (not shown) may be provided along the vertical edge of the mirror proximate to the hinge 24 where buildup of bacteria is most likely and manual maintenance may be most problematic, the additional UV-LED strip serving to sanitize bacteria that may have attached to the surface of the hinge since the hinge is not always as easily manually cleaned or sanitized, the action of the UV-LED strip ensures that the hinge remains bacteria free with or without manual maintenance. Suitable heat sinks may be provided to prevent excessive heat from developing in the UV-LED strips to promote reliability and longevity of the UV-LED strips by preventing excessive heat buildup.

Figure 4:
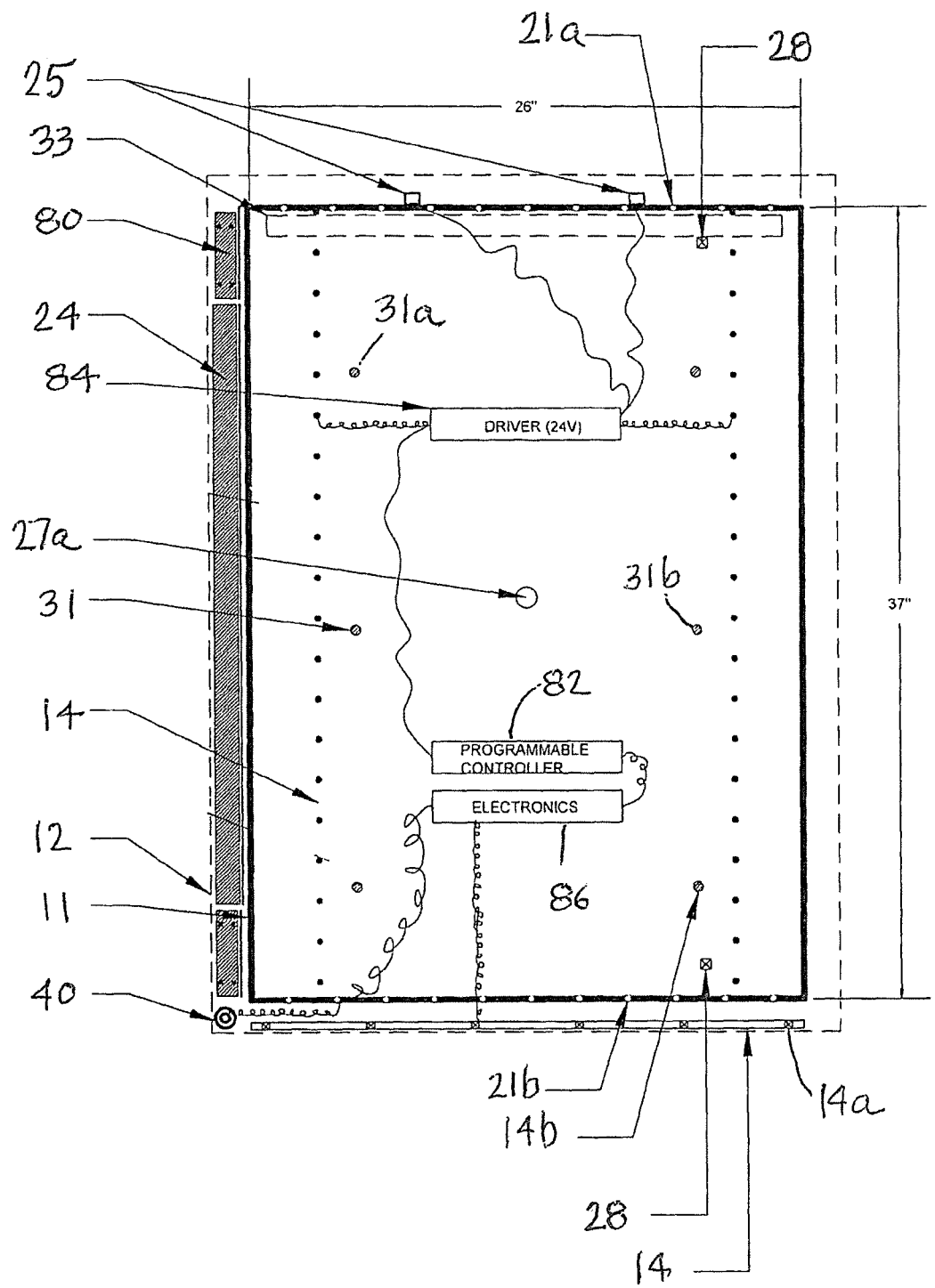
FIG. 4 is similar to FIG. 3 with the mirror panel removed to expose interior electronics including LED light strips, UV light strips, both inside and outside the cabinet, exhaust fans and control circuitry.
Figure 9:
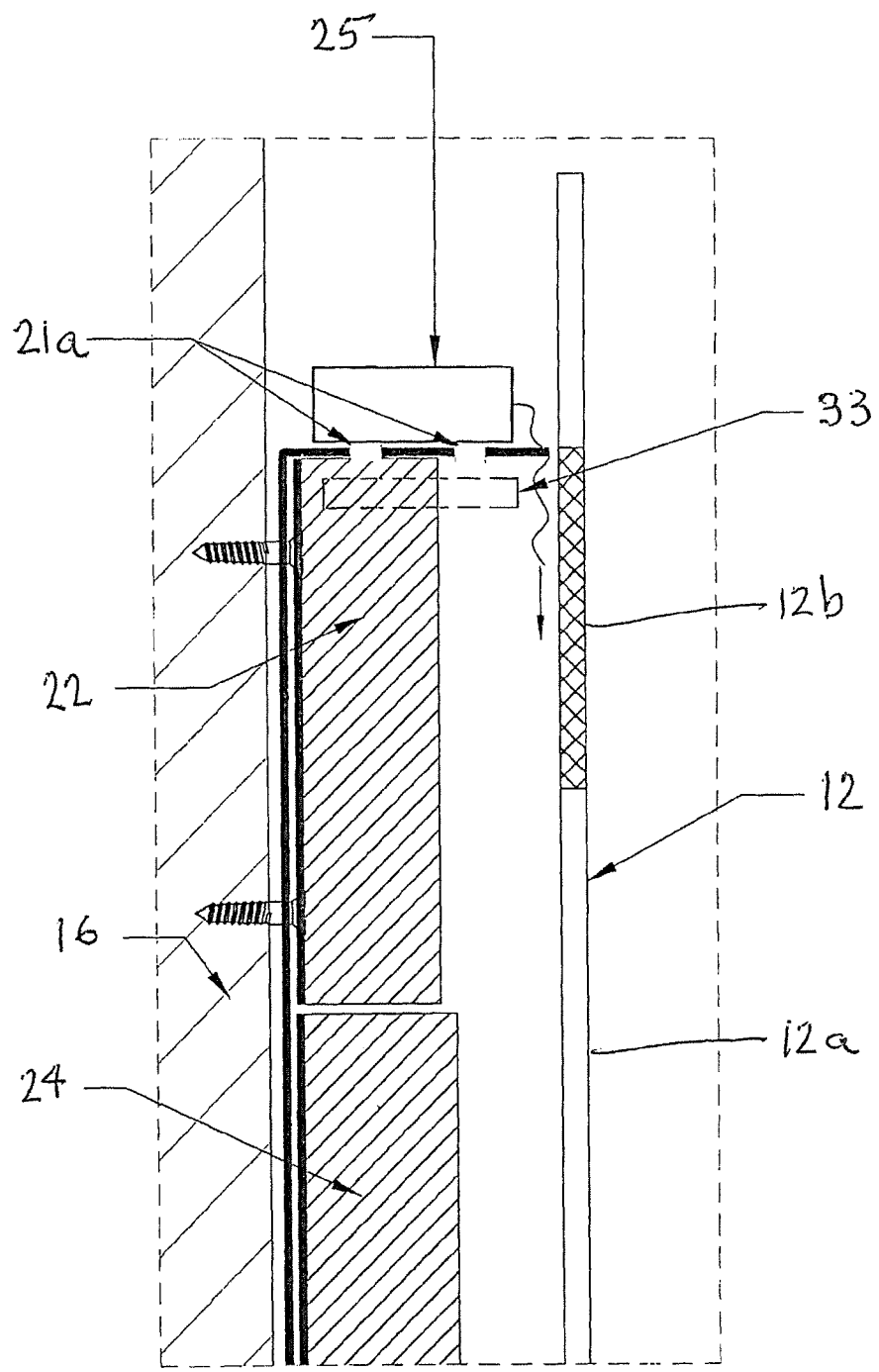
FIG. 9 is an enlarged view of detail C shown in FIG. 7.

Another important feature of the invention is the provision providing at least one UV light source 31 within the enclosed space 13. A plurality of such UV light sources may be provided within the enclosed space. FIG. 4, interior spaced UV light sources may be arranged in columns represented by light sources 31*a*, 31*b*, however, the specific arrangement of the internal UV light sources is not critical a plurality of substantially vertical columns of spaced UV light LEDs or other light sources may be provided as the light sources are arranged to expose the interior surfaces, including any shelving, within the cabinet 11. As shown in FIG. 4, the two columns of spaced UV light sources are positioned to be generally in close proximity to the corners at the lateral sides of the cabinet as opposed to the corner regions that may be more susceptible for buildup of pathogens.

The UV-LED strips may be replaced by UV mercury lamps or bulbs in the form of miniature florescent tubes that can be mercury lamps, xenon lamps or any lamp with UV wave generating components, waves or light. The invention contemplates the use of any UV source that generates suitable UV light behind a mirror in order to disinfect the area behind the mirror as well as in proximity to the mounting hinge.

In order to promote or enhance the flow of air 20 (FIG. 2) through the enclosed space or plenum 13 and exposing the air flow to the internal UV light sources 31, the top and bottom walls 11*a*, 11*b* are advantageously provided with air passageways 21 to allow vertical air flow through the enclosed space 13 along the vertical direction when the cabinet is mounted on a wall as shown. The passageways may be in the form of a plurality of openings or perforations 21*a*, 21*b*. Advantageously, in order to promote or enhance air flow through the enclosed space 13 one or more fans can be used to create a lower than atmospheric pressure above the top wall 11*a* or higher than atmospheric pressure above the bottom wall 11*b*. In FIG. 4, two micro exhause fans 22 are provided above the top wall 11*a* in registry with at least some of the perforations 21*a*. Any other means can be used to achieve such result.

In view of the foregoing, the present invention broadly contemplates an electric backlit mirror that is attached to a wall with a hinge for ease of movement to expose and disinfect the interior surfaces in the cabinet as well as surfaces below the cabinet 11. In this connection the driver, electronics, LED diodes, UV diodes, UV light bulbs, tubes or lamps may all be mounted on the mirror itself, allowing the wall behind the mirror to be free of any attachments other than the metal angle that carries the mirror. This facilitates and promotes the manual disinfecting of the entire wall behind the mirror where bacteria is likely to deposit.

Figure 12:
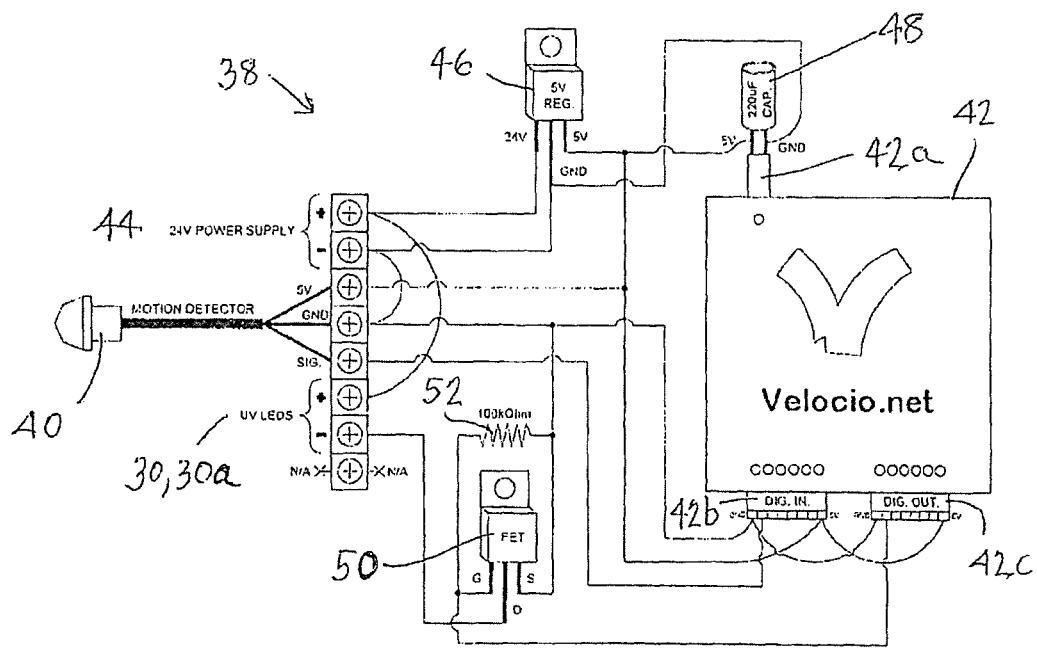
FIG. 12 is a schematic diagram of a motion control wiring circuit that can be used in connection with the aforementioned disinfecting vanity mirror embodiments for controlling or limiting excess emission of UV light to protect individuals in proximity to the mirrors.

To avoid potential safety issues to patients and occupants of the enclosures in which the mirrors are mounted from excessive exposure to UV light the mirrors of the invention may be provided with circuitry for intermittently de-activating or interrupting the UV light sources or generators so that these are not always on to emit UV light continuously but intermittently but sufficiently to be effective for sanitizing or disinfecting the areas within the enclosure. Referring to FIG. 12, a circuit 38 is shown that can be used for this purpose. The circuit 38 is preferably also mounted behind the mirror, possibly encapsulated, to minimize the openings, traps or surface areas on which bacteria can settle and grow. Circuit 38 serves two purposes. The first is to cycle the UV light sources (e.g. 30 and 30*a*) in accordance with a desired or predetermined schedule, and the second is to detect motion within the enclosure where the mirror is mounted so that the UV light sources can be de-activated, interrupted or de-energized when motion in proximity to the mirror is detected. Any programmed controller can be used to provide these functions. Circuit 38, by way of example, illustrates the use of a motion detector 40 connected to a programmed controller 42. A power supply 44, such as a 24 volt source, is used to energize the circuit 38, a 5 volt regulator being used, if necessary, to generate a regulated voltage to power the programmed controller 42. A capacitor 48 connected to the controller 42 at port 42*a*, a field effect transistor (FET) 50 and resistor 52 are connected to input port 42*b* and output port 42*c* of the programmed controller as shown. The UV LED light sources 30, 30*a* are connected as shown, the components connected to the programmed controller 42 enabling the controller 42 to operate as a timer to establish predetermined time intervals, as to be described in connection with FIG. 15. FIG. 14 however, is only one configuration of a programmed controller for timing the operation of the UV-LED's although any other known timers or timing circuits may be utilized for this purpose.

Figure 13:
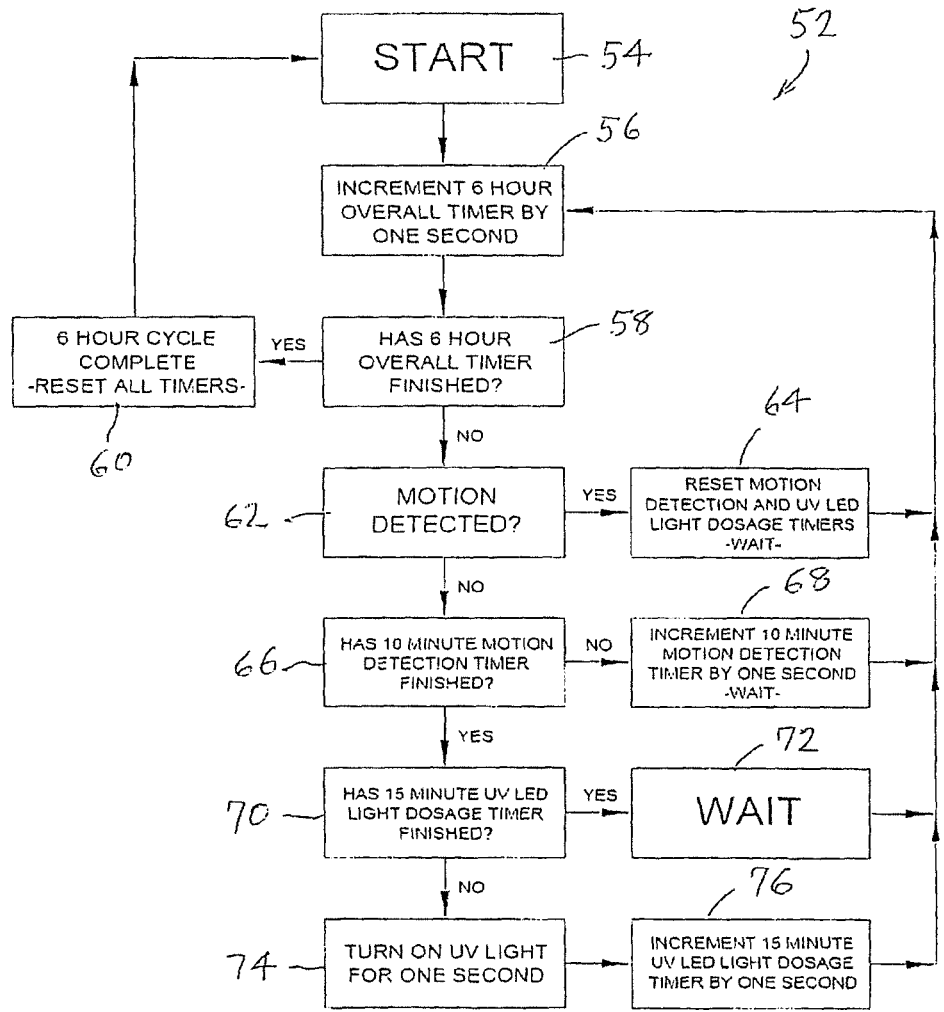
FIG. 13 illustrates a flow chart representing the operation of the programmed controller in FIG. 12 for controlling and preventing excess emission of UV light with the circuit shown in FIG. 12.

Referring to FIG. 13, a flow chart 52 is shown that illustrates the programmed protocol or logic for monitoring and controlling the UV light sources, whether they be LED's, lamps, bulbs, florescents, etc. Initially, the controller 42 commences operation at 54 to increment the timer in 6 hour intervals at 56. Thus, without external influences, the controller energizes the UV light sources every few hours. The UV light sources are energized several times during each 24 hour period. At 58, the controller 42 queries whether the timer has completed its programmed interval. After a 6 hour cycle has been completed all the timers are reset at 60 and the controller reverts to the start position at 54. If the 6 hour overall timer has not been completed the controller queries whether the motion detector 40 has detected any motion, at 62. If motion has been detected the motion detection and UV-LED light dosage timers are reset, at 64, and the controller reverts to incrementing the timer, at 56, to repeat the protocol. If motion has not been detected at 62 the controller queries whether a 10 minute motion detection timer has finished, at 66. If the motion detection timer has not finished the 10 minute motion detection timer is incremented by one second at 68 and the controller reverts to the programmed increment overall timer at 56. If the 10 minute motion detection timer has finished, at 66, the controller 42 queries whether the 15 minute UV-LED light dosage timer has finished, at 70. If it has finished the controller is instructed to wait, at 72, after which the hour is incremented by one second, at 56. If the 15 minute UV-LED light dosage timer has not finished, at 70, the UV light sources are turned on for one second, at 74. After the UV light has been activated, at 74, the 15 minute UV-LED timer is incremented by one second, at 76, and the 6 hour overall timer is thereafter incremented again at 56. The cycle is repeated on an ongoing or continuous basis with the program controller 42 regulating the operation or energization of the UV light sources at the preselected or desired time intervals, as may be modified by the presence of individuals sensed by the motion detector 40.

The mirror panel 12 is mounted on a cabinet "and at least one UV light source is mounted on the bottom end of the cabinet", the UV light source being configured to direct UV light vertically downwardly to sanitize air and surfaces below the mirror panel. The vanity mirror 10 is provided with a chassis hinge 80 that enables the pivoting of the cabinet to a position or juxtaposed against the mounting surface or wall in close proximity thereto as shown, for example, in FIGS. 18-21. However, the hinge 80 allows the cabinet 11 to be pivoted away from the wall mounting surface as shown in FIGS. 22 and 23 to provide access to the surface normally covered by the cabinet when in the closed position. This allows the surface behind the cabinet to be cleaned and disinfected periodically or as often as necessary. Referring to FIG. 17, with the mirror panel removed, a programmable controller 82 is connected to the LED light strips 14, controlled by the programmable controller 82. Electronics 86 shown in FIGS. 14 and 15 receive input from motion detector 40 and suitably actuates the UV LEDs or light source 30.

A feature of the invention is the provision of a metal flange or bracket 88 running along the bottom end or edge 11*b* of the cabinet 11 on which there are mounted UV LEDs, as shown in FIGS. 17 and 20-21. The number of the UV LEDs and the power of these LEDs are selected to provide the desired UV intensity on a countertop or surface C, keeping in mind that the UV intensity is inversely proposi-tional to the square of the distance, rapidly increasing at distances less than 1 meter. Directing the UV light downwardly or substantially downwardly increases the UV dose for effectiveness. Also, since dust and films that become deposited on the UV light sources lowers UV output these UV LEDs should normally be cleaned periodically. Also, a suitable fan or the like can be provided to blow air on the LEDs to keep them free of dust.

Referring to FIG. 17 a wall lock is provided for selectively maintaining the cabinet chassis in its closed or retracted position against the wall or mounting surface to prevent the cabinet to be inadvertently pivoted outwardly as shown in FIGS. 22 and 23.

Another feature of the invention is the provision of removable metal flange 88 shown in FIGS. 17, 20 and 21. The flange or bracket is generally L-shaped in cross section and extends substantially across the entire width of the bottom end 11*b* of the cabinet. The flange or bracket 88 has free edges 88*a* and 88*b* as shown in FIG. 21 and one UV light source including spaced UV LEDs are mounted generally along each of the free edges 88*a*, 88*b* of the flange or bracket 88. This ensures that the UV LEDs direct UV light substantially vertically downwardly to sanitize air and surfaces C below the vanity mirror.

Accordingly, the invention includes the following structural features:

A vanity mirror that can comprise a substantially enclosed cabinet having top, bottom and lateral ends and rear and front walls when mounted on a wall, the cabinet ends and the walls together forming a substantially enclosed space defining a vertical direction extending between the top and bottom ends, the front wall comprising a mirror panel that may be a backlit mirror. Mounting means is provided for mounting the cabinet on a wall and includes a hinge at one of the lateral ends to movably mount the cabinet for movement between a normally closed position substantially juxtaposed against the wall and an open position to provide access to a surface normally covered by the cabinet, when in the closed position, whereby the normally covered surface can be cleaned and disinfected.

The chassis hinge is connected to one of the cabinet lateral ends and connectable to a mounting surface, such as a wall.

A mirror hinge may be provided for pivotably mounting the mirror panel relative to the cabinet so that the mirror panel can be moved between a closed position to enclose the cabinet space and an open position to provide access to the cabinet space.

Preferably, the chassis and mirror hinges are arranged for independent pivotable movements.

At least one of the hinges may be formed of metal and/or at least one of said hinges may be formed of plastic.

The mirror hinge preferably pivotably mounts the mirror panel to the cabinet so that the mirror panel can be moved between a closed position to enclose the cabinet space and an open position to provide access to the cabinet space.

The chassis and mirror hinges may be connected to a common cabinet lateral end. According to a presently preferred embodiment the chassis hinge comprises two spaced hinges proximate to the top and bottom ends and the mirror hinge is arranged between the two spaced chassis hinges.

Preferably, the mirror panel is a backlit mirror provided with one or more light sources and a circuit is provided for energizing the mirror panel.

The method comprises providing a substantially enclosed cabinet having top, bottom and lateral ends and rear and front walls when mounted on a wall, the cabinet ends and the walls together forming a substantially enclosed space defining a vertical direction extending between the top and bottom ends, the front wall comprising a mirror panel. Pivotably or hingedly mounting the cabinet on a support surface, such as a wall, with a hinge at one of the lateral ends to movably mount the cabinet between a normally closed position substantially juxtaposed against the wall and an open position to provide access to a surface normally covered by the cabinet when in the closed position, whereby a normally covered support surface can be cleaned and/or disinfected.

A feature of the vanity mirror is that it can also include a magnetic or other wall lock for normally retaining the cabinet in the closed position and selectively enabling movement of the cabinet to an open position to expose the normally covered wall surface.

A plurality of UV light sources may also be provided within the enclosed space. The plurality of UV light sources can comprise UV LEDs spaced from each other along the vertical direction of the cabinet.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

The invention claimed is:

1. A vanity cabinet comprising a substantially enclosed housing having top, bottom and lateral ends and rear and front walls when mounted on a wall, said housing ends and said walls together forming a substantially enclosed space, said front wall comprising a mirror panel to open and close said vanity cabinet; mounting means for mounting said housing on a wall; a hinge at one of said lateral ends to movably mount said mirror panel for movement in relation to said housing; a first UV light source mounted within said housing to sanitize surfaces and objects within said storage cabinet when said door is in a closed position, said first UV light source comprising at least one substantially vertical column of spaced UV light emitters arranged to expose upper and lower interior surfaces of said storage cabinet to UV light; at least one second UV light source mounted on said bottom end of said housing, said at least one second UV light source being configured to direct UV light at least substantially vertically downwardly to sanitize air and surfaces below said vanity cabinet; and electrical control means for selectively energizing said first and second UV light sources.

2. A vanity cabinet as defined in claim 1, further comprising means for energizing at least said first UV light source upon closure of said mirror panel.

3. A vanity cabinet as defined in claim 1, wherein said plurality of UV light emitters comprise UV LEDs spaced from each other along said vertical direction.

4. A vanity cabinet as defined in claim 1, further comprising a flange or bracket extending generally along said bottom end, and at least one second UV light source is mounted on said flange or bracket.

5. A vanity cabinet as defined in claim 4, wherein said flange or bracket is removably attached to said bottom end of said vanity cabinet.

6. A vanity cabinet as defined in claim 1, wherein said first UV light source comprises two substantially vertical columns of spaced UV light emitters.

7. A vanity cabinet as defined in claim 1, wherein said two vertical columns substantially parallel and spaced from each other.

8. A vanity cabinet as defined in claim 1, wherein said first UV light source comprises at least one central UV light emitter substantially midway between said top and bottom ends and at least one UV light emitter between said central light emitter and said top end and at least one UV light emitter between said central light emitter and said bottom end.

9. A vanity cabinet as defined in claim 1, wherein said UV light emitters comprise UV LEDs.

10. A vanity cabinet comprising a substantially enclosed housing having top, bottom and lateral ends and rear and front walls when mounted on a wall, said housing ends and said walls together forming a substantially enclosed space, said front wall comprising a mirror panel with portions thereof at least partially light transmissive to open and close said vanity cabinet; mounting means for mounting said housing on a wall; a hinge at one of said lateral ends to movably mount said mirror panel for movement in relation to said housing; lighting means for providing back lighting behind at least some of said mirror portions; a UV light source mounted within said housing to sanitize surfaces and objects within said storage cabinet when said door is in a closed position, said UV light source comprising at least one substantially vertical column of spaced UV light emitters arranged to expose upper and lower interior surfaces of said storage cabinet to UV light; and electrical supply means for selectively energizing said UV light source.

11. A vanity cabinet as defined in claim 10, further comprising at least one second UV light source mounted on said bottom end of said housing, the UV light source being configured to direct UV light at least substantially vertically downwardly to sanitize air and surfaces below said storage cabinet.

* * * * *